(12) United States Patent
On et al.

(10) Patent No.: US 12,262,874 B2
(45) Date of Patent: Apr. 1, 2025

(54) ENDOSCOPE CONTROL DEVICE, METHOD OF CHANGING WAVELENGTH CHARACTERISTICS OF ILLUMINATION LIGHT, AND INFORMATION STORAGE MEDIUM

(71) Applicant: OLYMPUS CORPORATION, Tokyo (JP)

(72) Inventors: Seigo On, Hachioji (JP); Yasunori Morita, Hachioji (JP); Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 655 days.

(21) Appl. No.: 17/494,096

(22) Filed: Oct. 5, 2021

(65) Prior Publication Data

US 2022/0022739 A1 Jan. 27, 2022

Related U.S. Application Data

(63) Continuation of application No. PCT/JP2019/015752, filed on Apr. 11, 2019.

(51) Int. Cl.
*A61B 1/06* (2006.01)
*A61B 1/04* (2006.01)
*A61B 1/273* (2006.01)

(52) U.S. Cl.
CPC .......... *A61B 1/0638* (2013.01); *A61B 1/042* (2013.01); *A61B 1/0669* (2013.01); *A61B 1/2736* (2013.01)

(58) Field of Classification Search
None
See application file for complete search history.

(56) References Cited

U.S. PATENT DOCUMENTS

| | | | |
|---|---|---|---|
| 5,716,321 A | * | 2/1998 | Kerin ............... A61B 90/50 604/528 |
| 5,922,839 A | * | 7/1999 | Steiner ............ C07K 14/8142 530/324 |

(Continued)

FOREIGN PATENT DOCUMENTS

| | | |
|---|---|---|
| JP | 2012-045265 A | 3/2012 |
| JP | 2012-071007 A | 4/2012 |

(Continued)

OTHER PUBLICATIONS

International Search Report dated Jun. 25, 2019 received in PCT/JP2019/015752.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope apparatus includes comprises a processor. The processor causes the light source device to produce narrow band light as illumination light, and the narrow band light has a peak wavelength between a wavelength band including a local maximum of a hemoglobin absorption characteristic and a wavelength band including a local minimum of the hemoglobin absorption characteristic. The processor receives an image signal from the imaging device that outputs the image signal based on return light. The processor uses an image produced in response to the image signal to identify a state of the living body by identifying at least one of whether or not stomach mucosa is in a sterilized state, or whether or not the stomach mucosa is inflamed mucosa, outputs state identifying information indicating the state of the living body, and controls wavelength characteristics of the illumination light based on the state identifying information.

10 Claims, 8 Drawing Sheets

(56) References Cited

U.S. PATENT DOCUMENTS

| | | | |
|---|---|---|---|
| 6,172,215 B1* | 1/2001 | Keshi | C12Q 1/689 |
| | | | 435/6.15 |
| 9,582,900 B2* | 2/2017 | Moriya | G06T 7/90 |
| 2014/0320620 A1* | 10/2014 | Ikemoto | G06T 7/90 |
| | | | 348/71 |
| 2015/0193929 A1* | 7/2015 | Ikemoto | A61B 5/061 |
| | | | 382/128 |
| 2015/0238128 A1* | 8/2015 | Bechtold | A61B 5/1473 |
| | | | 600/309 |
| 2015/0269741 A1* | 9/2015 | Moriya | H04N 1/622 |
| | | | 382/164 |
| 2015/0269750 A1* | 9/2015 | Moriya | H04N 1/622 |
| | | | 382/128 |
| 2016/0007830 A1* | 1/2016 | Chun | A61B 1/000094 |
| | | | 600/476 |
| 2017/0032539 A1* | 2/2017 | Kuramoto | A61B 1/0005 |
| 2017/0049310 A1* | 2/2017 | Lepple-Wienhues | |
| | | | A61B 5/6815 |
| 2018/0289247 A1* | 10/2018 | Koshika | A61B 1/07 |
| 2018/0296281 A1* | 10/2018 | Yeung | A61B 34/32 |
| 2018/0368670 A1 | 12/2018 | Watanabe et al. | |
| 2019/0021580 A1* | 1/2019 | Mishima | A61B 1/0638 |
| 2019/0069769 A1 | 3/2019 | Kubo | |
| 2019/0122392 A1* | 4/2019 | Yamanashi | G06T 7/0012 |
| 2020/0118268 A1* | 4/2020 | Kuramoto | A61B 1/000094 |
| 2021/0052153 A1* | 2/2021 | Morita | A61B 1/000094 |
| 2021/0088772 A1* | 3/2021 | Morita | A61B 1/044 |
| 2021/0186315 A1* | 6/2021 | Oosake | A61B 1/000096 |
| 2021/0385367 A1* | 12/2021 | Yabe | A61B 1/0655 |
| 2022/0022739 A1* | 1/2022 | On | A61B 1/0669 |

FOREIGN PATENT DOCUMENTS

| | | |
|---|---|---|
| JP | 2012-152332 A | 8/2012 |
| JP | 2012-152333 A | 8/2012 |
| JP | 2014-166590 A | 9/2014 |
| WO | 2017/130325 A1 | 8/2017 |
| WO | 2017/170232 A1 | 10/2017 |
| WO | 2017/199509 A1 | 11/2017 |

* cited by examiner

ENDOSCOPE CONTROL DEVICE, METHOD OF CHANGING WAVELENGTH CHARACTERISTICS OF ILLUMINATION LIGHT, AND INFORMATION STORAGE MEDIUM

CROSS REFERENCE TO RELATED APPLICATION

This application is a continuation of International Patent Application No. PCT/JP2019/015752, having an international filing date of Apr. 11, 2019, which designated the United States, the entirety of which is incorporated herein by reference.

BACKGROUND

There are known methods for facilitating detection or diagnosis of a specific part with an endoscope apparatus by emitting special light including narrow band light or the like. A conventional technique using such special light is disclosed in Japanese Unexamined Patent Application Publication No. 2012-152333, for example. An endoscope system disclosed in Japanese Unexamined Patent Application Publication No. 2012-152333 analyzes image data of an observation image, determines a type of observed part based on a density of blood vessels in each layer of mucosa, and selects suitable illumination light corresponding to the determined type of observed part.

SUMMARY

In accordance with one of some aspect, there is provided an endoscope control device comprising a processor including hardware,
the processor being configured to:
cause a light source device to produce narrow band light as illumination light, the narrow band light having a peak wavelength between a wavelength band including a local maximum of a hemoglobin absorption characteristic and a wavelength band including a local minimum of the hemoglobin absorption characteristic;
receive an image signal from an imaging device that outputs the image signal based on return light; and
use an image produced in response to the image signal to identify a state of the living body by identifying at least one of whether or not stomach mucosa is in a sterilized state, or whether or not the stomach mucosa is inflamed mucosa, output state identifying information indicating the state of the living body, and control wavelength characteristics of the illumination light based on the state identifying information.

In accordance with one of some aspect, there is provided a method of changing wavelength characteristics of illumination light, the method comprising:
producing narrow band light as illumination light emitted to determine a state of a living body, the narrow band light having a peak wavelength between a wavelength band including a local maximum of a hemoglobin absorption characteristic and a wavelength band including a local minimum of the hemoglobin absorption characteristic;
outputting an image signal based on return light;
using an image produced in response to the image signal to identify the state of the living body by identifying at least one of whether or not stomach mucosa is in a sterilized state, or whether or not the stomach mucosa is inflamed mucosa, and outputting state identifying information indicating the state of the living body; and
changing, based on the state identifying information, wavelength characteristics of the illumination light emitted to determine the state of the living body.

In accordance with one of some aspect, there is provided a non-transitory information storage medium storing a program that causes a computer to execute steps of:
causing a light source device to produce narrow band light as illumination light, the narrow band light having a peak wavelength between a wavelength band including a local maximum of a hemoglobin absorption characteristic and a wavelength band including a local minimum of the hemoglobin absorption characteristic;
causing an imaging device to output an image signal based on return light;
using an image produced in response to the image signal to identify a state of the living body by identifying at least one of whether or not stomach mucosa is in a sterilized state, or whether or not the stomach mucosa is inflamed mucosa, and outputting state identifying information indicating the state of the living body; and
controlling wavelength characteristics of the illumination light based on the state identifying information.

DESCRIPTION OF EXEMPLARY EMBODIMENTS

Figure 1:
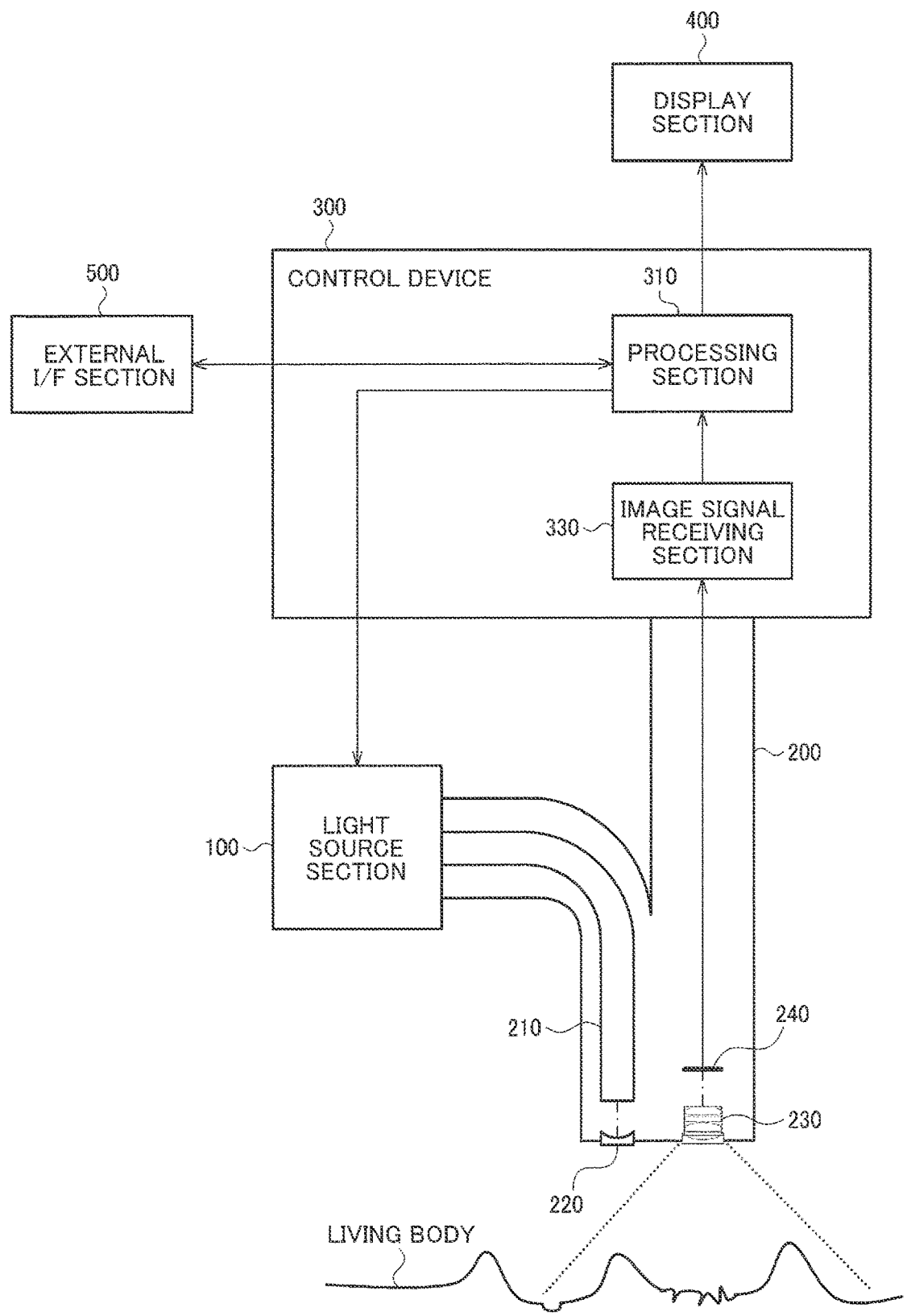
FIG. 1 illustrates a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is a configuration example of an endoscope apparatus. The endoscope apparatus includes an imaging section 200, a control device 300, a display section 400, an external I/F section 500, and a light source section 100. The endoscope apparatus may include a flexible scope used for a digestive tract or the like and a rigid scope used for a laparoscope or the like, for example. However, the endoscope apparatus is not limited to these.

The light source section 100 is a device configured to produce illumination light. The light source section 100 is also referred to as a light source device. The light source section 100 produces white light and special light as the illumination light. Specifically, the light source section 100 produces the white light in a white light imaging (WLI) mode and the special light in a special light mode. The special light mode is, for example, a narrow band imaging (NBI) mode using illumination light including blue narrow band light and green narrow band light. Emission timing of the illumination light may be set according to either a simultaneous method in which a plurality of light sources are caused to emit light simultaneously, or a frame sequential method in which the plurality of light sources are caused to emit light sequentially.

The imaging section 200 is inserted into a living body to capture an image of an object. The imaging section 200 is also referred to as a scope. The imaging section 200 includes a light guide 210, an illumination lens 220, an objective lens 230, and an image sensor 240. The image sensor 240 is also referred to as an image sensor. The imaging section 200 includes a connector, not illustrated, to be detachable from/attachable to the control device 300.

The light guide 210 guides the illumination light emitted from the light source section 100 to a distal end of the imaging section 200. The illumination lens 220 outputs the illumination light guided by the light guide 210 to the object. The object in the present embodiment is a living body. For example, the object to be observed with an endoscope apparatus for an upper digestive tract is mucosa of the stomach, gullet, or the like. Reflected light from the object enters the objective lens 230. An object image is formed by the objective lens 230 and captured by the image sensor 240.

The image sensor 240 captures the image of return light from the object irradiated with the illumination light, and outputs an image signal. The image sensor 240 may be either a color image sensor including color filters for respective pixels or a monochrome image sensor. For example, the color image sensor is a Bayer image sensor including color filters in a Bayer array, or a complementary color image sensor including complementary color filters.

The imaging section 200 includes an A/D conversion circuit. The A/D conversion circuit performs an analog to digital conversion to convert an analog image signal received from the image sensor 240 into a digital image signal. The A/D conversion circuit is included in the image sensor 240, for example.

The control device 300 performs signal processing including image processing. The control device 300 also controls each section of the endoscope apparatus. The control device 300 is also referred to as a processing device or a processor. The control device 300 includes a processing section 310 and an image signal receiving section 330. The processing section 310 is also referred to as a processing circuit or a processor.

The image signal receiving section 330 receives the image signal from the image sensor 240. For example, the image signal receiving section 330 is a connector configured to connect the imaging section 200 and the control device 300, an interface circuit configured to receive the image signal, a preprocessing circuit configured to generate image data from the image signal, or the like. The image signal receiving section 330 and the processing section 310 may each be implemented by individual hardware or may be implemented by integrated hardware.

The processing section 310 performs the image processing based on the image signal received by the image signal receiving section 330 so as to produce a display image, and outputs the display image to the display section 400. The processing section 310 also controls each section of the endoscope apparatus. Specifically, the processing section 310 controls wavelength characteristics of the illumination light, emission timing of a light source, and image capturing timing of the image sensor 240. For example, a user operates the external I/F section 500 to switch the mode between the WLI mode and the special light mode. When the special light mode is set, for example, the processing section 310 instructs the light source section 100 to produce the special light, produces a special light image in response to the image signal, and outputs the special light image to the display section 400. When the WLI mode is set, the processing section 310 instructs the light source section 100 to produce the white light, produces a white light image in response to the image signal, and outputs the white light image to the display section 400.

The display section 400 is a device configured to display the display image output from the processing section 310. The display section 400 is a liquid crystal display device, for example. The external I/F section 500 is a device configured to receive operation from the user to the endoscope apparatus. For example, the external I/F section 500 includes a button, a dial, a pointing device, a touch panel, or a foot switch.

2. Light Source Section

The following describes a case where a special light observation is performed by NBI. However, a method of the present embodiment can be applied to special light observations performed by other than NBI. That is, the method similar to the method of the present embodiment can be applied to a case where a histological change occurs to a predetermined portion and this changes a scattering state of the illumination light at the predetermined portion.

Figure 2:
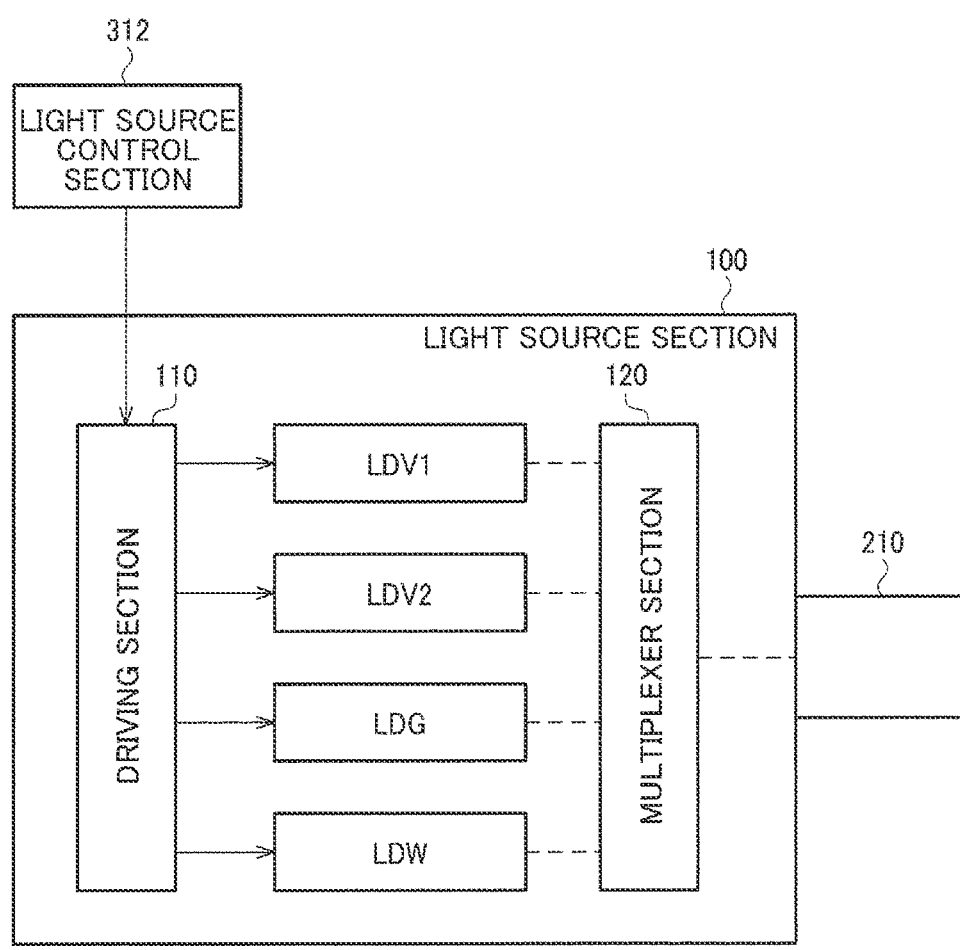
FIG. 2 illustrates a detailed configuration example of a light source section.

FIG. 2 is a detailed configuration example of the light source section 100. The light source section 100 includes a driving section 110, light sources LDV1, LDV2, LDG, and LDW, and a multiplexer section 120.

The driving section 110 receives input of a control signal instructing the emission timing and light amount of each light source from a light source control section 312. As will be described later referring to FIG. 5, the light source control section 312 is included in the processing section 310. The driving section 110 drives the light sources LDV1, LDV2, LDG, and LDW based on the control signal from the light source control section 312. For example, the driving section 110 supplies the light sources with driving currents to cause the light sources to emit light.

Each of the light sources LDV1, LDV2, LDG, and LDW produces light having a predetermined wavelength characteristic. The light sources LDV1, LDV2, and LDG produce first narrow band light, second narrow band light, and third narrow band light, respectively. A half-value width of each narrow band light is in a range from a few nm to some tens nm, for example. The light source LDW produces the white light. The white light has a continuous spectrum in a visible light band. Alternatively, the white light may include light in multiple bands. Each of the light sources is an LED or a laser, for example. Alternatively, the light source LDW of the white light may be a xenon lamp or the like. Each of the light sources LDV1, LDV2, and LDG may be implemented by a white light source and an optical filter that allows the corresponding narrow band light to pass through.

The multiplexer section 120 multiplexes light emitted from the light sources LDV1, LDV2, LDG, and LDW to input the multiplexed light to the light guide 210. The multiplexer section 120 includes dichroic mirrors and a lens, for example. Alternatively, the multiplexer section 120 may be an optical fiber to which the light is input from a plurality of input ends to be output from a single output end.

Figure 3:
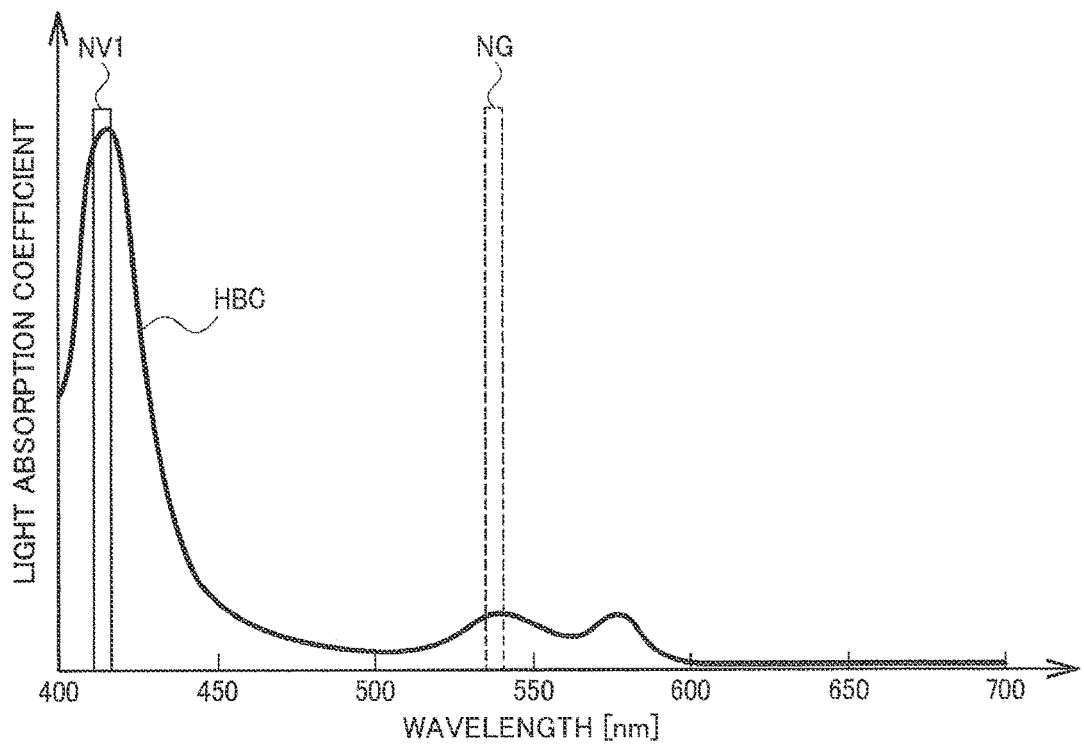
FIG. 3 illustrates an example of wavelength characteristics of narrow band light produced by the light source section.
Figure 4:
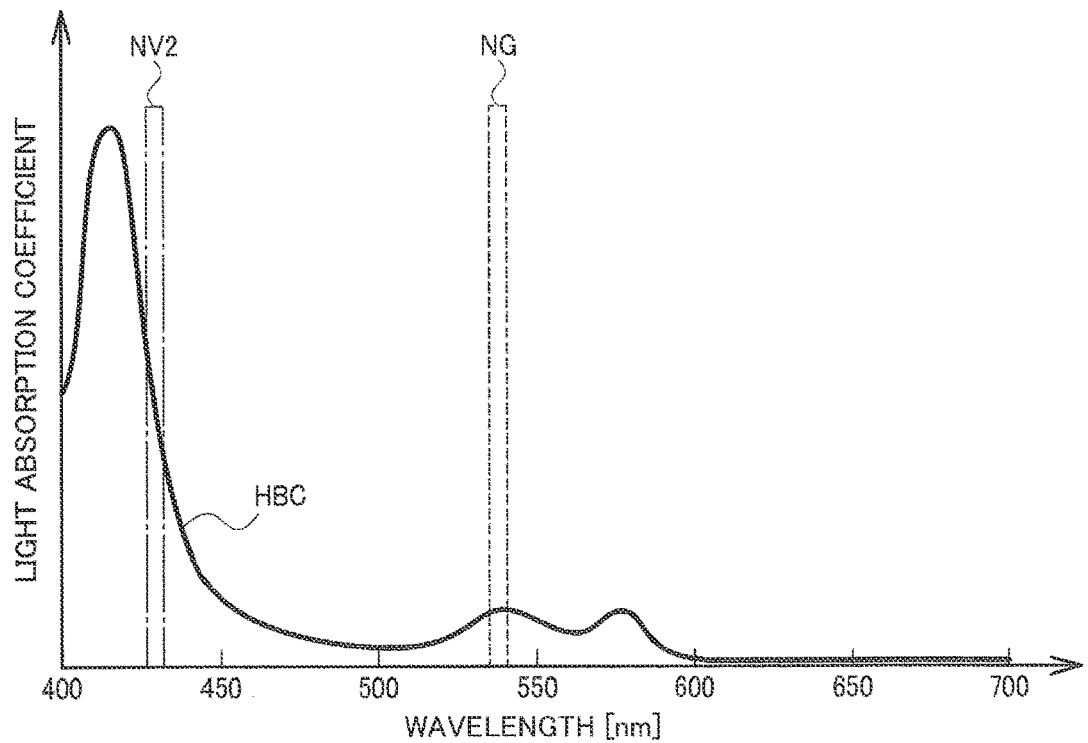
FIG. 4 illustrates an example of wavelength characteristics of narrow band light produced by the light source section.

FIGS. 3 and 4 are examples of wavelength characteristics of the narrow band light produced by the light source section 100. FIG. 3 is the example of the wavelength characteristics when the light sources LDV1 and LDG emit light, and FIG. 4 is the example of the wavelength characteristics when the light sources LDV2 and LDG emit light.

The light source section 100 produces the narrow band light having a peak wavelength between a wavelength band including a local maximum of a hemoglobin absorption coefficient HBC and a wavelength band including a local minimum of the hemoglobin absorption coefficient HBC. The local maximum of the absorption coefficient HBC is around the wavelength of 415 nm and the local minimum is around the wavelength of 500 nm. The wavelength band including the local maximum is a predetermined wavelength range including the local maximum, and the wavelength band including the local minimum is a predetermined wavelength range including the local minimum. The wavelength band from the wavelength band including the local maximum to the wavelength band including the local minimum is from 400 to 520 nm, for example.

Specifically, the light sources LDV1 and LDV2 produce first narrow band light NV1 and second narrow band light NV2, respectively. When the visible light band is divided into a blue band, green band, and red band, the first narrow band light NV1 has a peak wavelength in the blue band. The second narrow band light NV2 has a peak wavelength in a band longer than that of the first narrow band light in the blue band. In the examples in FIGS. 3 and 4, the first narrow band light NV1 has the peak wavelength of 415 nm, and the second narrow band light NV2 has the peak wavelength of 430 nm. The peak wavelength of 415 nm of the first narrow band light NV1 corresponds to a peak wavelength of blue narrow band light used in normal NBI. The peak wavelength of 430 nm of the second narrow band light NV2 corresponds to what the peak wavelength of 415 nm of the first narrow band light NV1 is shifted to a long wavelength side. The peak wavelength of the first narrow band light NV1 may be in a range from 400 to 420 nm, and the peak wavelength of the second narrow band light NV2 may be in a range from 420 to 450 nm.

The light source LDG produces third narrow band light NG. The third narrow band light NG has a peak wavelength in the green band. In the example of FIG. 4, the third narrow band light NG has the peak wavelength of 540 nm. The peak wavelength of 540 nm of the third narrow band light NG corresponds to a peak wavelength of green narrow band light used in normal NBI. The peak wavelength of the third narrow band light NG may be in a range from 530 to 550 nm. A light amount ratio between the first narrow band light NV1 and the third narrow band light NG and a light amount ratio between the second narrow band light NV2 and the third narrow band light NG may be set arbitrarily.

Figure 5:
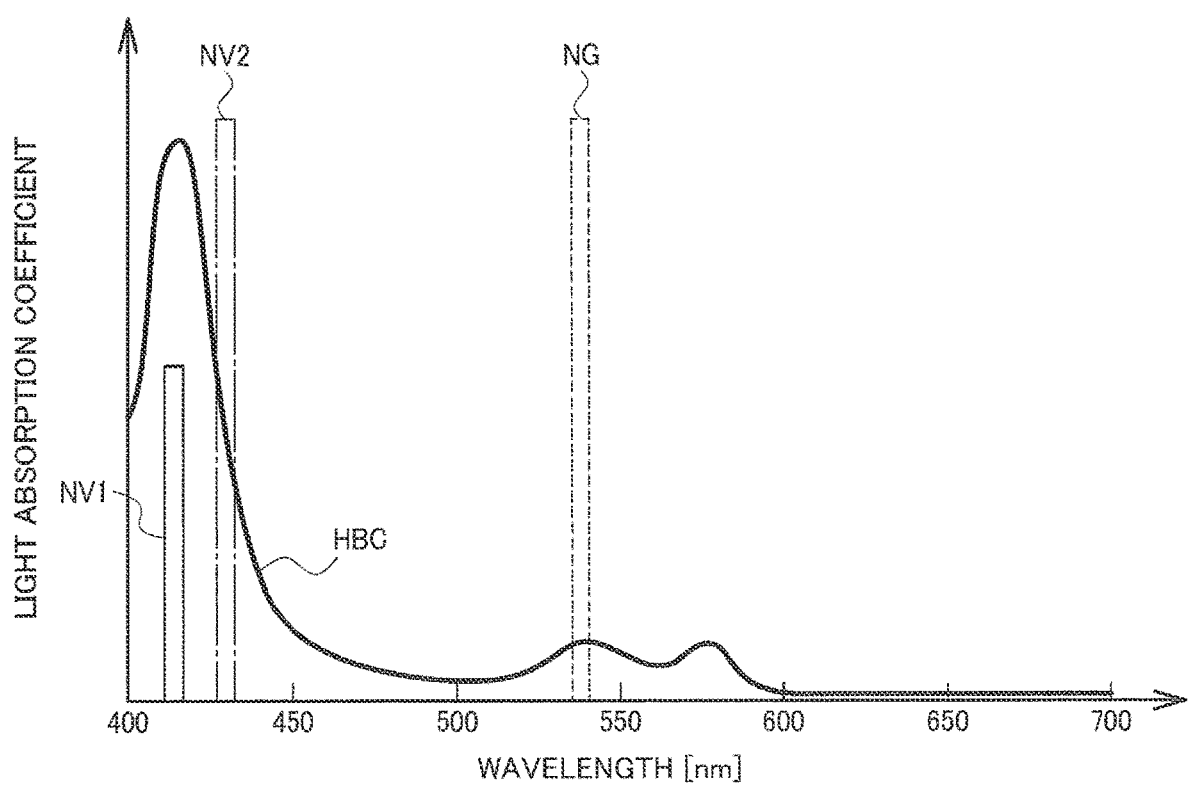
FIG. 5 illustrates an example of wavelength characteristics of narrow band light produced by the light source section.

FIG. 5 is an example of wavelength characteristics when the light sources LDV1, LDV2, and LDG emit light. Assume that a weight coefficient of a light amount of the second narrow band light NV2 with respect to a light amount of the first narrow band light NV1 is a. A light amount ratio of the light amount of the first narrow band light NV1 to the light amount of the second narrow band light NV2 is $(1-\alpha):\alpha$, and $\alpha$ is a real number satisfying a relation of $0 \leq \alpha \leq 1$. The light source control section 312 controls the weight coefficient $\alpha$ to control the light amount ratio between the first narrow band light NV1 and the second narrow band light NV2. FIG. 3 shows a case of $\alpha=0$, and FIG. 4 shows a case of $\alpha=1$. That is, light emission control by weighting includes a case when the first narrow band light NV1 or the second narrow band light NV2 is off.

In accordance with the present embodiment described above, the first narrow band light NV1 and the second narrow band light NV2 having the peak wavelength in the band longer than that of the first narrow band light are used. The second narrow band light NV2 has a longer wavelength than the wavelength of the first narrow band light NV1, so that a scattering degree in tissue is smaller than a scattering degree of the first narrow band light NV1, and thus the second narrow band light NV2 reaches deeper below a tissue surface than the first narrow band light NV1. With two kinds of narrow band light having different scattering degrees, suitable illumination can be performed even when scattering states before and after the histological change are different. The following describes this along with the description of operation of the processing section 310.

3. Processing Section

Figure 6:
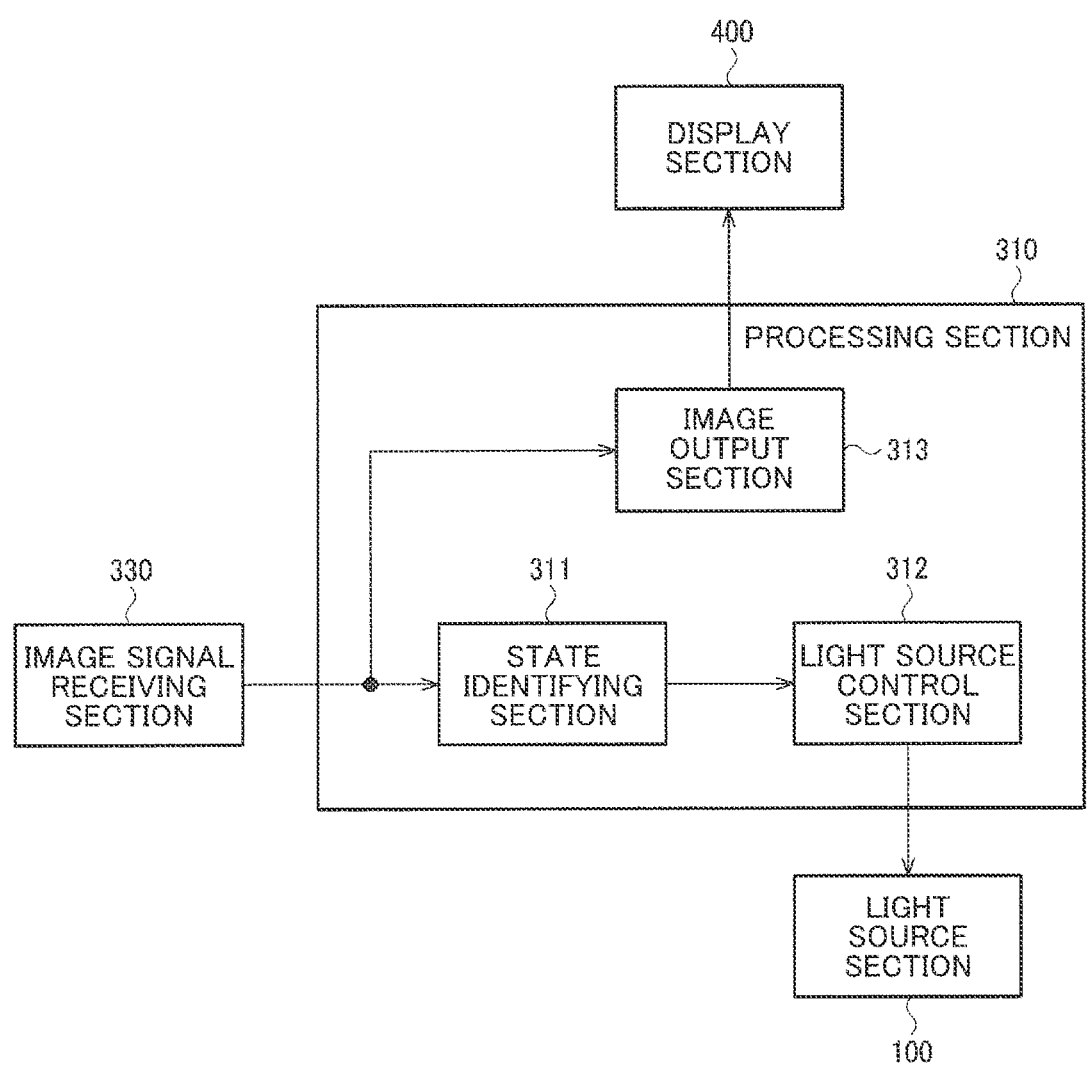
FIG. 6 illustrates a detailed configuration example of a processing section.

FIG. 6 is a detailed configuration example of the processing section 310. The processing section 310 includes a state identifying section 311, the light source control section 312, and an image output section 313.

The state identifying section 311 identifies a state of a living body from an image produced in response to the image signal, and outputs a result as state identifying information. The state identifying section 311 may produce an image for an identifying process, or may use an image produced by the image output section 313. The light source control section 312 controls the wavelength characteristics of the illumination light based on the state identifying information. Specifically, the light source control section 312 switches the light between the first narrow band light NV1 and the second narrow band light NV2 as illustrated in FIGS. 3 and 4. Alternatively, the light source control section 312 changes the weighting between the first narrow band light NV1 and the second narrow band light NV2 as illustrated in FIG. 5.

As a result, the state identifying section 311 can identify which of the states the object is in, before or after the histological change, even when the scattering states before and after the histological change are different. Accordingly, the light source control section 312 can control the wavelength characteristics of the illumination light based on a result of the identification. Consequently, illumination suitable for the state of the living body can be performed. Specifically, when a target object is hard to be seen due to the change in the scattering state, changing the wavelength of the narrow band light can change the degree of the scattering. As a result, visibility of the target object can be restored.

As described referring to FIG. 3 and so forth, the narrow band light has the peak wavelength between the wavelength band including the local maximum of a hemoglobin absorption characteristic and the wavelength band including the local minimum of the hemoglobin absorption characteristic. That is, the peak wavelength of the narrow band light is controlled in the wavelength band where hemoglobin absorption is relatively high. The target object is an object including hemoglobin, and a representative example is a blood vessel. With the narrow band light, a blood vessel image at a depth corresponding to the peak wavelength of the narrow band light can be captured. However, a change in the light scattering state reduces the visibility of the blood vessel image. At this time, changing the peak wavelength allows the light to reach the blood vessel, which can improve the visibility of the blood vessel image.

The state of the living body described here means a state of a portion of the same kind and a state where at least a light scattering intensity changes before and after a state change. More specifically, the state of the living body means a state having a histological change before and after the state change. The histological change may include a change in the thickness of tissue, or a change in intercellular junction of tissue, for example.

The state identifying information is information indicating the identified state of the living body. For example, the state identifying section 311 identifies the state from a plurality of options of states, and outputs a flag, an index, identification data, or the like indicating the identified state as the state identifying information.

Furthermore, in accordance with the present embodiment, the first narrow band light NV1 has the peak wavelength in the blue band, and the second narrow band light NV2 has the peak wavelength in the band longer than that of the first narrow band light NV1. That is, the light source control section 312 shifts the peak wavelength in the blue band to the long wavelength side to control the wavelength characteristics of the illumination light.

Since the first narrow band light NV1 has the peak wavelength in the blue band, a blood vessel image in a surface layer of tissue such as a mucosal surface layer can be captured. However, when the scattering intensifies due to a histological change, the scattering may attenuate a contrast of the blood vessel image, or the scattering light may make a lesion look similar to another type of lesion.

In accordance with the present embodiment, when the scattering is relatively intense, the light can be shifted to the second narrow band light NV2 having the scattering degree lower than the scattering degree of the first narrow band light NV1. As a result, the illumination light reaches the blood vessel in a depth where the illumination light should normally reach, and thus the contrast of the blood vessel image can be improved, or the type of lesion or the like can be easily determined.

Furthermore, in accordance with the present embodiment, the peak wavelength of the first narrow band light NV1 is in the range from 400 to 420 nm. The state identifying section 311 uses the image captured using at least the first narrow band light NV1 and the third narrow band light NG to identify whether stomach mucosa is in a sterilized state.

Since the wavelength between 400 to 420 nm is close to the local maximum of the hemoglobin absorption coefficient HBC, the first narrow band light NV1 can be used to capture an image of the blood vessel in the surface layer of the mucosa or the like with high contrast. With the first narrow band light NV1 and the third narrow band light NG, the special light observation called NBI can be implemented.

Although NBI is used for diagnosing stomach cancer, visibilities of the stomach cancer before and after sterilization of *Helicobacter pylori* are different. Specifically, generation of the histological change in the stomach mucosa by the sterilization raises the scattering degree of the first narrow band light NV1 in the stomach mucosa, so that the first narrow band light NV1 barely reaches the blood vessel in the surface layer. In addition, although an inflammation of the stomach mucosa looks to be a white zone in NBI, the stomach cancer after the sterilization may falsely look to be the white zone. The white zone is a region that looks whiter than surrounding regions. Seeing the white zone, physicians suspect the inflammation of the stomach mucosa, which complicates distinction between the stomach cancer after the sterilization and the inflammation.

In accordance with the present embodiment, when the state identifying section 311 identifies that the stomach mucosa is in the sterilized state, the light source control section 312 can cause the second narrow band light NV2 having the wavelength longer than that of the first narrow band light NV1 to be produced. As a result, the second narrow band light NV2 reaches the blood vessel in the surface layer, and the visibility of the stomach cancer after the sterilization can be improved.

Furthermore, in accordance with the present embodiment, as will be described later referring to FIG. 8, the light source section 100 may produce first illumination light including the narrow band light and second illumination light of the white light. The state identifying section 311 may identify the state of the living body from the image captured using the second illumination light, and the light source control section 312 may control the wavelength characteristics of the first illumination light based on the state identifying information.

As a result, the state of the living body can be accurately identified when identifying the state of the living body is easier with the white light image. Accordingly, the wavelength of the special light is controlled in accordance with the result of the identification, so that the wavelength suitable for the state of the living body can be selected with higher accuracy.

Furthermore, in accordance with the present embodiment, as will be described later referring to FIG. 8, the state identifying section 311 may identify inflamed mucosa. That is, the state identifying section 311 may identify whether an inflammation is present in mucosa shown in an image.

The light scattering is more intense in the inflamed mucosa than in normal mucosa, so that the inflamed mucosa looks to be the white zone in the NBI observation. This attenuates the visibility of the blood vessel or lesion present under the inflamed mucosa. Since the inflamed mucosa looks to be a region with strong redness in the white light image, the inflamed mucosa can be identified from the color or the like in the image. Upon detection of the inflamed mucosa, the light source control section 312 causes the second narrow band light NV2 to be emitted so that the second narrow band light NV2 can reach under the inflamed mucosa. As a result, the visibility of the blood vessel or lesion present under the inflamed mucosa can be improved in the NBI observation.

Furthermore, in accordance with the present embodiment, when the state identifying section 311 detects that the state of the living body is in a first state, the light source control section 312 sets the weight coefficient α to a first weight coefficient. As described referring to FIG. 5, α is the weight coefficient of the light amount of the second narrow band light NV2 with respect to the light amount of the first narrow band light NV1. When the state identifying section 311 detects that the state of the living body is in a second state different from the first state, the light source control section 312 sets the weight coefficient α to a second weight coefficient higher than the first weight coefficient. The second state is a state where the scattering of the illumination light in the mucosa of the living body is more intense than in the first state.

As a result, upon detection of the second state where the scattering of the illumination light in the mucosa is relatively intense, the weight of the second narrow band light NV2 on the long wavelength side can be raised. This reduces the scattering degree of the narrow band light in the mucosa, so that the visibility of the blood vessel in the surface layer or the like can be secured in the second state as well as in the first state.

Furthermore, in accordance with the present embodiment, as will be described later referring to FIG. 9, the state identifying section 311 may estimate a proximity degree between the imaging section 200 and the living body. The light source control section 312 may control the wavelength characteristics of the illumination light based on the state identifying information and the proximity degree. The proximity degree is a distance between a distal end of the scope and a surface of the object. For example, the proximity degree is estimated from a focus position of the objective lens 230, a zoom magnification of the objective lens 230, or the like.

Physicians perform screening while moving the scope in the living body. Upon detection of a region suspected to be a lesion or the like in the screening, the physicians closely observe the region by bringing the scope near the region. In accordance with the present embodiment, the wavelength characteristics of the illumination light is controlled using the proximity degree, so that wavelength control corresponding to an observation state is enabled. For example, normal NBI may be performed in the screening regardless of the state of the living body, and the weight coefficient α of the second narrow band light NV2 may be raised upon detection of a predetermined state, such as the sterilized mucosa or the like, in the close observation.

As for a method by which the state identifying section 311 identifies the state of the living body, an identifying method using an image recognition algorithm or an identifying method using machine learning such as artificial intelligence (AI) can be employed.

The image recognition algorithm detects the state of the living body based on a feature amount of an image or a shape of an object, for example. The feature amount is a color or luminance of the image, for example. The shape of the object is a blood vessel structure or a mucosal surface structure, for example. The mucosal surface structure is an atrophy of stomach mucosa or a shape of a lesion such as a polyp, for example.

In the machine learning, a training model learns with training data including training images of the living bodies and true labels added to the training images. The true labels are made by physicians or the like. For example, the true labels include a label indicating whether the stomach mucosa has been sterilized, a label indicating whether an inflammation is present in the mucosa, or the like. The training model includes an inference algorithm and a parameter. The inference algorithm may be any one of various types of machine learning algorithms such as a neural network or a support vector machine. The parameter is used in the inference algorithm, and is a weight coefficient between nodes in the neural network, for example. The training model that has finished learning is referred to as a trained model.

The state identifying section 311 uses the trained model to identify the state of the living body from the image. The trained model may be implemented as a program or hardware. When the trained model is implemented as the program, the processor executes the program to implement a function of the state identifying section 311.

The image output section 313 produces the display image in response to the image signal, and outputs the display image to the display section 400. In the WLI mode, an R channel, G channel, and B channel of the image signal are input to an R channel, G channel, and B channel of the display image, respectively. In the NBI mode, the B channel of the image signal is input to the B channel and G channel of the display image, and the G channel of the image signal is input to the R channel of the display image. When the image sensor 240 is a color image sensor, the image output section 313 also performs an interpolation process. The mode between the WLI mode and the NBI mode may be set by a user through the external I/F section 500, or may be set correspondingly to the proximity degree between the scope and the object, for example, as will be described referring to FIG. 9. The image output section 313 produces the display image based on the set mode.

The control device 300 including the processing section 310 may be configured as described below. The control device 300 includes a memory configured to store information, and a processor configured to operate based on the information stored in the memory. The information includes, for example, a program and various data. The processor includes hardware. The processor identifies the state of the living body from the image produced in response to the image signal, outputs the state identifying information indicating the state of the living body, and controls the wavelength characteristics of the illumination light based on the state identifying information.

The processor may have functions of sections each implemented by individual hardware, or the functions of sections each implemented by integrated hardware, for example. For example, the processor may include hardware, and the hardware may include at least one of a circuit that processes a digital signal and a circuit that processes an analog signal. For example, the processor may include one or more circuit devices mounted on a circuit board, or one or more circuit elements. The one or more circuit devices include an IC, for example. The one or more circuit elements include a resistor or a capacitor, for example. The processor may be a central processing unit (CPU), for example. However, the processor is not limited to the CPU, and may be any one of various other processors such as a graphics processing unit (GPU) or a digital signal processor (DSP). Alternatively, the processor may be an integrated circuit device such as an application specific integrated circuit (ASIC) or a field programmable gate array (FPGA). The processor may include an amplifier circuit, a filter circuit, or the like that processes an analog signal.

The memory may be a semiconductor memory such as an SRAM or a DRAM, or may be a register. The memory may be a magnetic storage device such as a hard disk drive, or may be an optical storage device such as an optical disk device. For example, the memory stores a computer-readable instruction, and each function of the processing section 310 is implemented as a process when the processor executes the instruction. The instruction used here may be an instruction set that is included in a program, or may be an instruction that instructs the hardware circuit included in the processor to operate.

Furthermore, the program that implements the process performed by the processing section 310 can be stored in a computer-readable information storage medium, for example. The information storage medium can be implemented by an optical disk, a memory card, an HDD, or a semiconductor memory (such as a ROM), for example. The semiconductor memory is a ROM, for example. The processing section 310 performs various processes in accordance with the present embodiment based on the program and data stored in the information storage medium. That is, the information storage medium stores the program that causes a computer to function as the processing section 310. The computer is a device including an input device, a processing section, a storage section, and an output section.

Procedures of the processes performed by the processing section 310 are described below referring to flowcharts in FIGS. 7 to 9. The following describes an example that the first narrow band light NV1 and the second narrow band light NV2 are switched in accordance with the state of the living body. However, the light amount ratio between the first narrow band light NV1 and the second narrow band light NV2 may be switched in accordance with the state of the living body.

Figure 7:
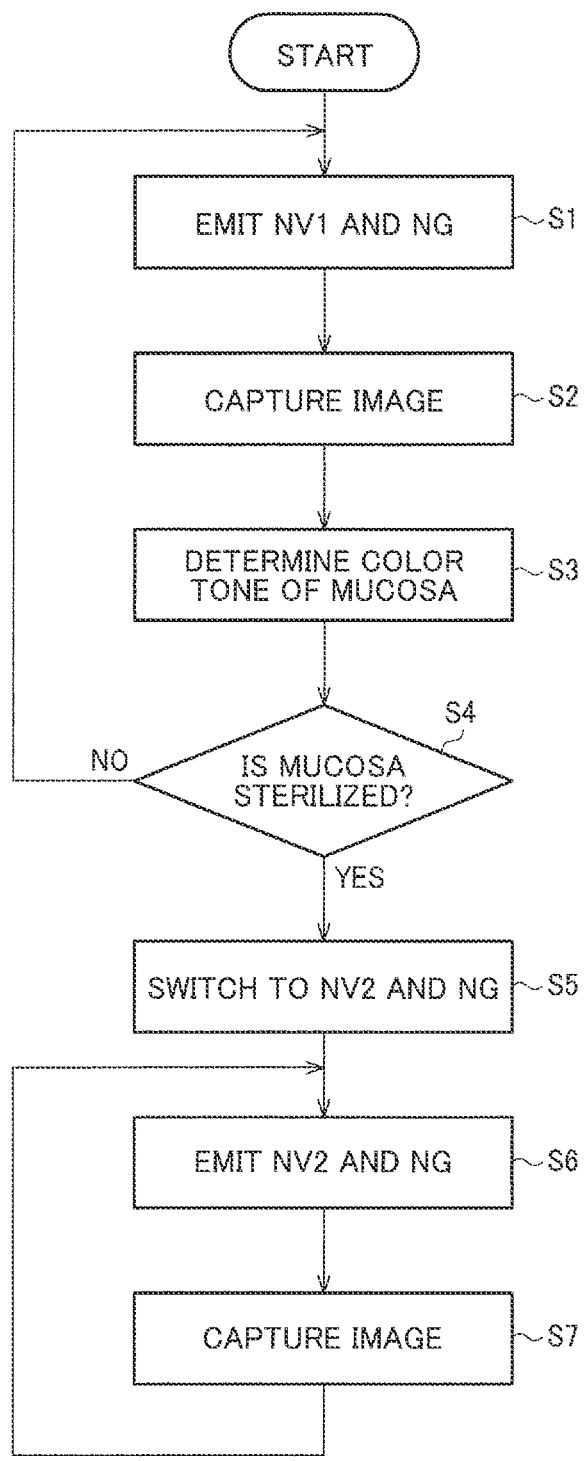
FIG. 7 is a flowchart illustrating procedures of processes performed by the processing section.

FIG. 7 is a flowchart illustrating procedures when the state of the living body is identified in the NBI observation.

In a step S1, the light source control section 312 causes the light source section 100 to emit the first narrow band light NV1 and the third narrow band light NG. In a step S2, the image sensor 240 captures an image, and the image signal receiving section 330 receives the image signal.

In a step S3, the state identifying section 311 determines a color tone of mucosa from the image. Specifically, the state identifying section 311 determines whether whiteness of the white zone is present in the NBI image. In a step S4, the state identifying section 311 identifies whether the mucosa has been sterilized based on a result of the determination of the color tone. Since the stomach cancer falsely looks to be the white zone in the sterilized mucosa, detection of the white zone enables identification of the sterilized mucosa. In the steps S3 and S4, the state identification may be performed using the machine learning.

When it is identified in the step S4 that the mucosa has not been sterilized, the steps S1 to S4 are performed again. When it is identified in the step S4 that the mucosa has been sterilized, the light source control section 312 switches the setting of the wavelength characteristics to the second narrow band light NV2 and the third narrow band light NG in a step S5. In a step S6, the light source control section 312 causes the light source section 100 to emit the second narrow band light NV2 and the third narrow band light NG. In a step S7, the image sensor 240 captures an image, the image signal receiving section 330 receives the image signal, and the process returns to the step S6.

Figure 8:
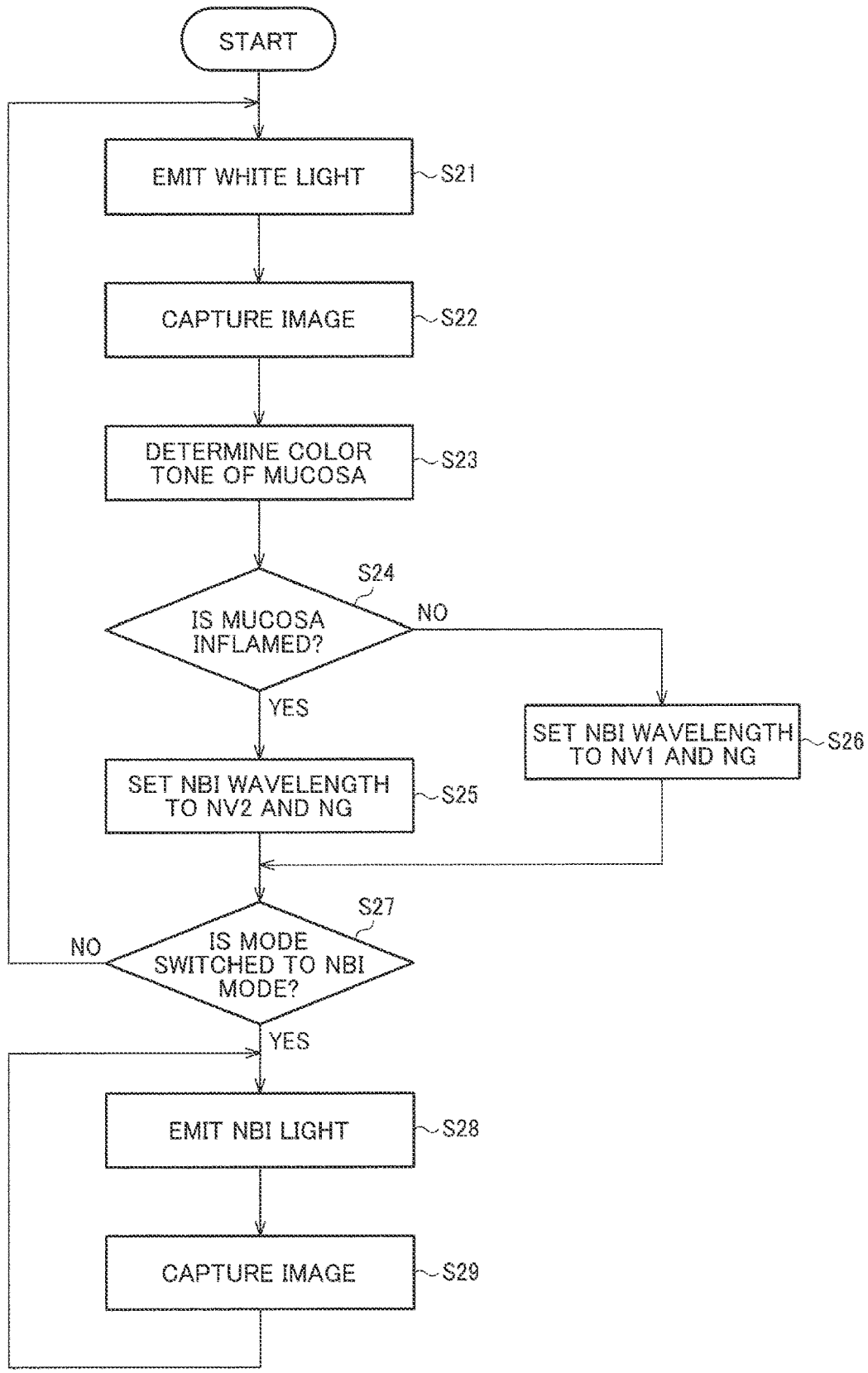
FIG. 8 is a flowchart illustrating procedures of processes performed by the processing section.

FIG. 8 is a flowchart illustrating procedures when the state of the living body is identified in the WLI observation.

In a step S21, the light source control section 312 causes the light source section 100 to emit the white light. In a step S22, the image sensor 240 captures an image, and the image signal receiving section 330 receives the image signal.

In a step S23, the state identifying section 311 determines the color tone of mucosa from the image. Specifically, the state identifying section 311 determines whether redness of inflamed mucosa is present in the white light image. In a step S24, the state identifying section 311 identifies whether the mucosa is inflamed based on a result of the determination of the color tone. In the steps S23 and S24, the state identification may be performed using the machine learning.

When it is identified in the step S24 that the mucosa is inflamed, the light source control section 312 sets the wavelength characteristics in the NBI mode to the second narrow band light NV2 and the third narrow band light NG in a step S25. When it is identified in the step S24 that the mucosa is not inflamed, the light source control section 312 sets the wavelength characteristics in the NBI mode to the first narrow band light NV1 and the third narrow band light NG in a step S26.

In a step S27, the light source control section 312 determines whether the mode is switched from the WLI mode to the NBI mode. Specifically, the light source control section 312 determines whether operation for switching the mode to the NBI mode is performed through the external OF section 500.

When it is determined in the step S27 that the mode is in the WLI mode, the process returns to the step S21. When it is determined in the step S27 that the mode is switched to the NBI mode, the light source control section 312 causes, in a step S28, the light source section 100 to emit the narrow band light in accordance with the wavelength characteristics set in the steps S25 or S26. In a step S29, the image sensor 240 captures an image, the image signal receiving section 330 receives the image signal, and the process returns to the step S28.

Figure 9:
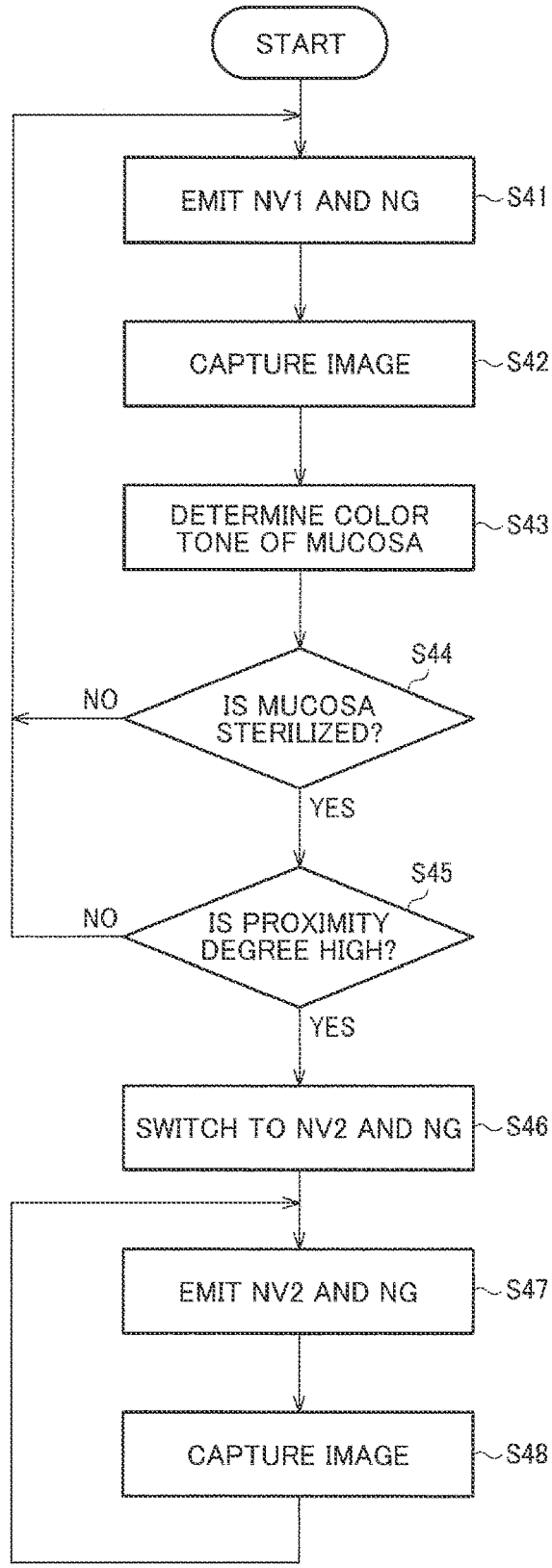
FIG. 9 is a flowchart illustrating procedures of processes performed by the processing section.

FIG. 9 is a flowchart illustrating procedures when the wavelength characteristics is switched based on the state identifying information and the proximity degree.

In a step S41, the light source control section 312 causes the light source section 100 to emit the first narrow band light NV1 and the third narrow band light NG. In a step S42, the image sensor 240 captures an image, and the image signal receiving section 330 receives the image signal.

In a step S43, the state identifying section 311 determines the color tone of mucosa from the image. In a step S44, the state identifying section 311 identifies whether the mucosa has been sterilized based on the result of the determination of the color tone.

When it is identified in the step S44 that the mucosa has not been sterilized, the steps S41 to S44 are performed again. When it is identified in the step S44 that the mucosa has been sterilized, the light source control section 312 determines whether the distal end of the scope and the object are close in a step S45. For example, the focus position or the zoom magnification of the objective lens 230 is operated through the external I/F section 500. The light source control section 312 determines the proximity degree based on the focus position or the zoom magnification set by this operation.

When it is determined in the step S45 that the distal end of the scope and the object are not close, the steps S41 to S44 are performed again. When it is determined in the step S45 that the distal end of the scope and the object are close, the light source control section 312 switches the setting of the wavelength characteristics in the NBI mode to the second narrow band light NV2 and the third narrow band light NG in a step S46. In a step S47, the light source control section 312 causes the light source section 100 to emit the second narrow band light NV2 and the third narrow band light NG. In a step S48, the image sensor 240 captures an image, the image signal receiving section 330 receives the image signal, and the process returns to the step S47.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope control device comprising:
a processor including hardware, the processor being configured to:
cause a light source device to produce illumination light including first narrow band light and second narrow band light, the first narrow band light and the second narrow band light having peak wavelengths between a wavelength band including a local maximum of a hemoglobin absorption characteristic and a wavelength band including a local minimum of the hemoglobin absorption characteristic, and the peak wavelength of the second narrow band light being a band longer than the peak wavelength band of the first narrow band light;
receive an image signal from an imaging device that outputs the image signal based on return light;
use an image produced in response to the image signal to identify a state of a living body by identifying at least one of whether stomach mucosa is in a state in which sterilization has not been performed or a state after sterilization has been performed, or whether or not the stomach mucosa is inflamed mucosa;
output state identifying information indicating the state of the living body; and
control wavelength characteristics of the illumination light based on the state identifying information, to:
set a first weight coefficient as a weight coefficient of a light amount of the second narrow band light with respect to a light amount of the first narrow band light upon detection that the state of the living body is in a first state; and
set a second weight coefficient larger than the first weight coefficient as the weight coefficient upon detection that the state of the living body is in a second state different from the first state.

2. The endoscope control device as defined in claim 1, wherein the peak wavelength of the first narrow band light is in a blue band.

3. The endoscope control device as defined in claim 2, wherein:
the processor is configured to cause the light source device to produce the illumination light further including third narrow band light having a peak wavelength in a green band; and
the peak wavelength of the second narrow band light is between the peak wavelength of the first narrow band light and a peak wavelength of the third narrow band light.

4. The endoscope control device as defined in claim 3, wherein the processor is configured to use an image captured using at least the first narrow band light and the third narrow band light to identify the state of the living body by identifying whether or not the stomach mucosa is in the state in which sterilization has not been performed or the state after sterilization has been performed.

5. The endoscope control device as defined in claim 2, wherein the peak wavelength of the first narrow band light is in a range from 400 to 420 nm.

6. The endoscope control device as defined in claim 1,
wherein the illumination light is first illumination light, and
wherein the processor is configured to:
cause the light source device to produce the first illumination light and second illumination light including white light;
use an image captured using the second illumination light to identify the state of the living body; and
control wavelength characteristics of the first illumination light based on the state identifying information.

7. The endoscope control device as defined in claim 1, wherein the second state is a state where scattering of the illumination light in mucosa of the living body is more intense than in the first state.

8. The endoscope control device as defined in claim 1, wherein the processor is configured to:
estimate a proximity degree between the imaging device and the living body; and
control the wavelength characteristics of the illumination light based on the state identifying information and the proximity degree.

9. A method comprising:
causing a light source device to produce illumination light including first narrow band light and second narrow band light, the first narrow band light and the second narrow band light having peak wavelengths between a wavelength band including a local maximum of a hemoglobin absorption characteristic and a wavelength band including a local minimum of the hemoglobin absorption characteristic, and the peak wavelength of the second narrow band light being a band longer than the peak wavelength band of the first narrow band light;
receiving an image signal from an imaging device that outputs the image signal based on return light;
using an image produced in response to the image signal to identify a state of a living body by identifying at least one of whether stomach mucosa is in a state in which sterilization has not been performed or a state after sterilization has been performed, or whether or not the stomach mucosa is inflamed mucosa;
outputting state identifying information indicating the state of the living body; and
controlling wavelength characteristics of the illumination light based on the state identifying information, to:
set a first weight coefficient as a weight coefficient of a light amount of the second narrow band light with respect to a light amount of the first narrow band light upon detection that the state of the living body is in a first state; and
set a second weight coefficient larger than the first weight coefficient as the weight coefficient upon detection that the state of the living body is in a second state different from the first state.

10. A non-transitory information storage medium storing a program that causes a computer to at least execute:
causing a light source device to produce illumination light including first narrow band light and second narrow band light, the first narrow band light and the second narrow band light having peak wavelengths between a wavelength band including a local maximum of a hemoglobin absorption characteristic and a wavelength band including a local minimum of the hemoglobin absorption characteristic, and the peak wavelength of the second narrow band light being a band longer than the peak wavelength of the first narrow band light;

receiving an image signal from an imaging device that outputs the image signal based on return light;

using an image produced in response to the image signal to identify a state of a living body by identifying at least one of whether stomach mucosa is in a state in which sterilization has not been performed or a state after sterilization has been performed, or whether or not the stomach mucosa is inflamed mucosa;

outputting state identifying information indicating the state of the living body; and controlling wavelength characteristics of the illumination light based on the state identifying information, to:

set a first weight coefficient as a weight coefficient of a light amount of the second narrow band light with respect to a light amount of the first narrow band light upon detection that the state of the living body is in a first state; and set a second weight coefficient larger than the first weight coefficient as the weight coefficient upon detection that the state of the living body is in a second state different from the first state.

\* \* \* \* \*